US011006937B2

(12) United States Patent
Nativ et al.

(10) Patent No.: US 11,006,937 B2
(45) Date of Patent: May 18, 2021

(54) SURGICAL DELIVERY DEVICES FOR MELTABLE BONE WAX OR BONE PUTTY

(71) Applicant: Ethicon, Inc., Somerville, NJ (US)

(72) Inventors: Nir I. Nativ, West Orange, NJ (US); Thomas C. Weindl, Bedminster, NJ (US); Leo B. Kriksunov, Ithaca, NY (US)

(73) Assignee: Ethicon, Inc., Somerville, NJ (US)

( * ) Notice: Subject to any disclaimer, the term of this patent is extended or adjusted under 35 U.S.C. 154(b) by 42 days.

(21) Appl. No.: 16/261,678

(22) Filed: Jan. 30, 2019

(65) Prior Publication Data
US 2020/0237356 A1 Jul. 30, 2020

(51) Int. Cl.
A61B 17/00 (2006.01)
A61B 17/88 (2006.01)
A61L 24/08 (2006.01)
A61L 24/00 (2006.01)

(52) U.S. Cl.
CPC .... A61B 17/00491 (2013.01); A61B 17/8822 (2013.01); A61L 24/08 (2013.01); A61B 2017/005 (2013.01); A61B 2017/00548 (2013.01); A61B 2017/00734 (2013.01)

(58) Field of Classification Search
CPC .......... A61B 17/00491; A61B 17/8805; A61B 50/30; A61B 2017/005; A61B 17/8822; A61B 2017/00548; A61B 2017/00734; A61L 24/08
USPC .............................................. 606/92, 93, 94
See application file for complete search history.

(56) References Cited

U.S. PATENT DOCUMENTS

| 4,439,420 | A | 3/1984 | Mattei et al. | |
| 5,514,135 | A * | 5/1996 | Earle | A61B 17/8822 222/389 |
| 6,783,534 | B2 | 8/2004 | Mehdizadeh | |
| 8,147,246 | B2 | 4/2012 | Neubardt | |
| 8,801,723 | B2 | 8/2014 | Shah et al. | |
| 2004/0230309 | A1* | 11/2004 | DiMauro | A61F 2/442 623/17.12 |

(Continued)

FOREIGN PATENT DOCUMENTS

| CN | 201431481 | 3/2010 |
| EP | 2506893 | 6/2011 |

OTHER PUBLICATIONS

National Center for Biotechnology Information. "PubChem Compound Summary for CID 10423, Oxetane" PubChem, https://pubchem.ncbi.nlm.nih.gov/compound/Oxetane. Accessed Aug. 27, 2020. (Year: 2004).*
Darensbourg, Donald J., et al. "Aliphatic Polycarbonates Produced from the Coupling of Carbon Dioxide and Oxetanes and Their Depolymerization via Cyclic Carbonate Formation." Macromolecules, vol. 44, No. 8, Mar. 24, 2011, pp. 2568-2576., doi:10.1021/ma2002323. (Year: 2011).*

(Continued)

Primary Examiner — Matthew J Lawson
Assistant Examiner — Lisa Nguyen
(74) Attorney, Agent, or Firm — David R. Crichton; Leo B. Kriksunov

(57) ABSTRACT

The present invention is directed to a device for delivering a sealant to a tissue, comprising a sealant compartment, a cooling gas compartment, and a heater, all disposed inside a unified housing; with heater configured for rendering the sealant liquid or semi-liquid or molten and flowable; with sealant compartment configured for expressing the sealant in a flowable form from device via an exit nozzle; with gas compartment configured for expressing a cooling gas via a gas expression port; with exit nozzle and gas expression port co-directed into the same direction.

19 Claims, 9 Drawing Sheets

(56) References Cited

U.S. PATENT DOCUMENTS

| | | | |
|---|---|---|---|
| 2008/0073448 A1* | 3/2008 | Kendall | B05C 5/02 239/337 |
| 2008/0167658 A1* | 7/2008 | Kerr | A61B 17/8822 606/93 |
| 2008/0214989 A1* | 9/2008 | Kawata | A61B 17/00491 604/24 |
| 2009/0220686 A1 | 9/2009 | Minion | |
| 2013/0131683 A1 | 5/2013 | Shah et al. | |
| 2014/0163519 A1* | 6/2014 | Shadduck | A61B 17/8827 604/506 |
| 2016/0074602 A1* | 3/2016 | Wang | A61M 5/48 604/518 |
| 2016/0278786 A1 | 9/2016 | Constantine | |

OTHER PUBLICATIONS

Darensbourg, Donald J., et al. "A Facile Catalytic Synthesis of Trimethylene Carbonate from Trimethylene Oxide and Carbon Dioxide." Green Chemistry, vol. 12, No. 8, Jul. 19, 2010, pp. 1376-1379., doi:10.1039/c0gc00136h. (Year: 2010).*

Dickenson, R.P. et al., "The Mechanical Properties of Bone in Osteoporosis", The Journal of Bone and Joint Surgery, 1981, 63-B(2): pp. 233-238.

Ciarallo, A. et al., "An approach to compare the quality of cancellous bone from the femoral necks of healthy and osteoporotic patients through compression testing and microcomputed tomography imaging", McGill Journal of Medicine, 2006, 9(2): pp. 102-107.

* cited by examiner

SURGICAL DELIVERY DEVICES FOR MELTABLE BONE WAX OR BONE PUTTY

FIELD OF THE INVENTION

This invention relates to devices for delivering a tissue sealant and more particularly to absorbable or non-absorbable sealing and/or hemostatic compositions for tissue and/or bone sealing, with delivery devices of the present invention providing heating and cooling of the sealant compositions during and after delivery. The compositions are solid or semi-solid at body temperature but are having putty-like or semi-liquid consistency at elevated temperature that is 5-50° C. higher than body temperature. This invention also relates to a process for applying the sealant.

BACKGROUND OF THE INVENTION

Various substances and compositions have been employed to control bleeding from cut bone surfaces. One class of materials used for the control of this type of hemorrhage is called bone wax. Bone waxes are used for controlling hemorrhages from the cut surfaces of bones, such as those of the ribs, by applying the wax as a putty over the cut surface so that the material mechanically occludes and seals the open ends of the bleeding osseous vessels. Bone waxes used in surgery are frequently prepared from refined beeswax which has been admixed with nonabsorbable and water insoluble hydrocarbons and vegetable oils. Some wax formulations can have relatively poor adhesion properties, and the hard brittle state of the wax at room temperatures may require softening and kneading prior to application.

U.S. Pat. No. 4,439,420 by Mattei, et al. titled "Absorbable hemostatic composition" discloses an absorbable hemostatic composition for use in the control of osseous hemorrhage, comprising: (i) a component (A) comprising either a biocompatible fatty acid salt alone, which comprises between 45% and 80% by weight based on the weight of the total composition; or a mixture of said fatty acid salt with a biocompatible in vivo absorption enhancing agent, in which said mixture comprises between 35% and 45% by weight of said fatty acid salt based on the weight of the total composition, and between 25% and 35% by weight of said absorption enhancing agent, based on the weight of the total composition; and (ii) a component (B) comprising a body absorbable biocompatible base selected from the group consisting of ethylene oxide/propylene oxide block copolymers, polyethylene glycols and methoxypolyethylene glycols, triglycerides and fatty acid esters, the cation of said fatty acid salt being selected from the group consisting of calcium, magnesium, zinc, aluminum, lithium and barium, the fatty acid anion being saturated or unsaturated and containing from 10 to 22 carbon atoms in the chain, said composition having a putty-like consistency at room temperature, and a tackiness sufficient for it to adhere readily to a bloody bone surface.

U.S. Pat. No. 8,801,723 titled "Minimally invasive surgical applicator", discloses an apparatus for the application of a surgical material or substance at an elevated temperature, comprising: a) an applicator body, said body comprising: (i) a rear grip, (ii) a chamber for receiving said surgical material or substance, wherein the chamber for receiving surgical material or substance comprises a cover, wherein the chamber cover is a hatch, and (iii) a bayonet; b) a trigger assembly, pivotally actuable on the applicator body; c) an extrusion rod for engagement with said applicator body; d) a tip attached to the bayonet, wherein the tip comprises an angle of inclination of between 0-45 degrees relative to longitudinal axis of the bayonet; and e) a heating assembly for warming the surgical material or substance above room temperature, wherein the heating assembly comprises a heating element and a power source operably connected to said heating element, wherein the heating element is disposed about or along at least 10 percent of the length of the bayonet.

Utility Model publication CN201431481Y "Detachable medical bone wax injection device/A detachable medical bone wax spraying device discloses a detachable medical bone wax spraying device, comprising a nozzle, a spring, an indicator lamp, a temperature sensor, a power supply, a sealing ring and sealing cushions, wherein the device is assembled by a melter and a pressurizer, which are connected with the nozzle in turn.

U.S. Patent Application publication No. 2016/0278786 titled "BONE WAX DISPENSER" discloses a dispenser comprising: a tubular housing; an adjustable base configured to move from one end of the tubular housing to a second end of the tubular housing; and bone wax disposed within the tubular housing.

European Patent Application publication EP2506893A2 titled "ADHESIVE DELIVERY DEVICES, SYSTEMS AND METHODS" discloses an adhesive material injection system for delivering adhesive to a patient site comprising: adhesive material; and a delivery device comprising: a housing; and a nozzle, said nozzle comprising a proximal end and a distal end wherein the adhesive material is configured to exit said nozzle distal end.

U.S. Patent Application publication No. 2009/0220686A1 titled "COMPRESSED AIR SPRAY GLUE GUN" discloses a spray gun for spraying an adhesive material comprising: an adhesive pathway for receiving the adhesive material; a heating element for melting the adhesive material into an adhesive stream which flows within the adhesive pathway; an air pathway for an air stream; and a nozzle comprising an end of the adhesive pathway and an end of the air pathway, wherein the adhesive pathway and the air pathway are configured at the nozzle such that the air stream and adhesive stream exit the nozzle in a substantially laminar direction relative to one another.

U.S. Patent Application publication No. 2008/0073448A1 titled "ANTI-STRINGING APPLICATOR" discloses an applicator for applying a substance, the applicator comprising: a nozzle adapted to deliver the substance; and a gas port configured to be enveloped by the substance and to deliver a gas flow to disrupt a flow of the substance.

U.S. Pat. No. 6,783,534 titled "Bone wax applicator" discloses a bone wax applicator, comprising means for providing a force, a cylinder having a piston end and an outlet end, a piston coupled to said means for providing a force and disposed within said cylinder for close sliding fit therein and for movement between said cylinder piston end and said cylinder outlet end in response to said force, said cylinder having an access opening, an access opening cover moveable between open and closed positions, an open wax transport tube connected at one end to said cylinder outlet end and having an opposing free end, said opposing free end having a discharge opening, and a dissector tip attached to said opposing free end adjacent said discharge opening.

U.S. Pat. No. 8,147,246 titled "Surgical bone wax applicator" discloses a surgical bone wax applicator, comprising: one or more layers of absorbent material; a mass of bone wax deposited on a surface of the absorbent material so that the bone wax adheres to the material; an electrical heating element comprising an electrically resistive heating wire or conductor that extends within the absorbent material in the vicinity of the mass of bone wax, and the heating wire has an associated pair of electrical contact terminals that are exposed on the applicator for connecting the heating wire to an outside voltage source; and the heating wire is constructed and arranged to heat and soften the mass of bone wax when the electrical contact terminals of the heating wire are connected to the outside voltage source and a determined current flows through the heating wire.

SUMMARY OF THE INVENTION

In one embodiment, the present invention relates to devices for delivering a sealant to a tissue, comprising: a sealant compartment, a cooling gas compartment, and a heater, all disposed inside a unified housing; said heater configured for rendering the sealant liquid or semi-liquid or molten and flowable; said sealant compartment configured for expressing the sealant in a flowable form from said device via an exit nozzle; said gas compartment configured for expressing a cooling gas via a gas expression port; said exit nozzle and said gas expression port co-directed to a first direction.

In some embodiments, the sealant comprises a wax, a hemostatic wax, a bone wax, a bone putty, and combinations thereof. In some embodiments, the sealant comprises polyethylene glycol, beeswax, calcium stearate, alkylene oxide copolymers, isopropyl palmitate, paraffin, petroleum jelly, oxidized regenerated cellulose powder (ORC), oxidized cellulose powder (OC), gelatin powder, starch powder, chitosan powder, and combinations thereof, and has a melting point from about 40° C. to about 100° C.

In some embodiments, the device is configured for hand-held operation with one hand. In some embodiments, the device further comprises a separator that is comprising a thin elongated strip extending from said housing and positioned between said sealant in said flowable form being expressed from said exit nozzle and said cooling gas being expressed via said gas expression port, wherein said separator extends distally from said housing beyond said exit nozzle and said gas expression port in said first direction.

In some embodiments, the cooling gas expressed via said gas expression port is configured for cooling and solidification of said molten sealant deposited on said tissue within 1-10 seconds.

In some embodiments, the device further comprises an actuator operatively connected to said sealant compartment and configured upon depressing to activate expressing the sealant via said exit nozzle; and a gas switch operatively connected to said gas compartment and configured for activating expressing said cooling gas via said gas expression port. In some embodiments, the actuator is operatively connected to said gas switch, wherein depressing said actuator simultaneously operates said gas switch, whereby said gas switch at least partially blocks expressing said cooling gas via said gas expression port. In some embodiments, half-pressing said actuator at least partially blocks expressing said cooling gas and full pressing said actuator activates expressing the sealant via said exit nozzle. In some embodiments, releasing said actuator simultaneously operates said gas switch, whereby said gas switch opens expressing said cooling gas via said gas expression port. In some embodiments, the actuator is normally closed and said gas switch is normally open.

In some embodiments, the present invention relates to methods of delivering the sealant to the tissue, comprising: Directing the device onto the tissue; optionally directing said cooling gas to said tissue and effecting pre-cooling of said tissue and removal of a pooled blood; Actuating delivery of said molten sealant to said tissue; Depositing said molten sealant onto said tissue; Optionally stopping delivering of said molten sealant to said tissue; Actuating delivery of said cooling gas to said molten sealant on said tissue; Cooling and solidifying said molten sealant on said tissue.

DETAILED DESCRIPTION OF THE INVENTION

According to embodiments of the present invention, absorbable or non-absorbable (or partially absorbable) sealing and/or hemostatic compositions are used for sealing tissue and/or bone. The compositions are solid or semi-solid at body temperature but are having putty-like or semi-liquid or fully liquid flowable consistency at elevated temperature that is 5-50° C. higher than body temperature. Exemplary compositions include waxes, such as beeswax, calcium stearate, alkylene oxide copolymers, and similar, and combinations thereof, optionally mixed with other agents such as isopropyl palmitate, paraffin, petroleum jelly, etc. Polyethylene glycol (PEG) based materials are especially useful, including polyethylene glycols (PEGs) of specific molecular weight, mixtures of PEGs of several molecular weights, and mixtures of one or more PEGs with additional agents, such as thickeners, diluents and powders.

One example of a suitable sealant is a PEG mixed with a hemostatic powder, such as oxidized regenerated cellulose powder (ORC), oxidized cellulose powder (OC), gelatin powder, starch powder and/or chitosan powder. Suitable PEGs can include, for example, PEG4000 that has a melting point of 53-58° C.; PEG10000 that has a melting point of 55-60° C.; PEG35000 that has a melting point of circa 60° C.

Generally any biocompatible meltable substance that forms a solid or semi-solid film at the body temperature i.e.

at 36-40° C., or generally below about 45 or 50° C., can be utilized as hemostatic and sealing agent according to the present invention.

Figure 1:
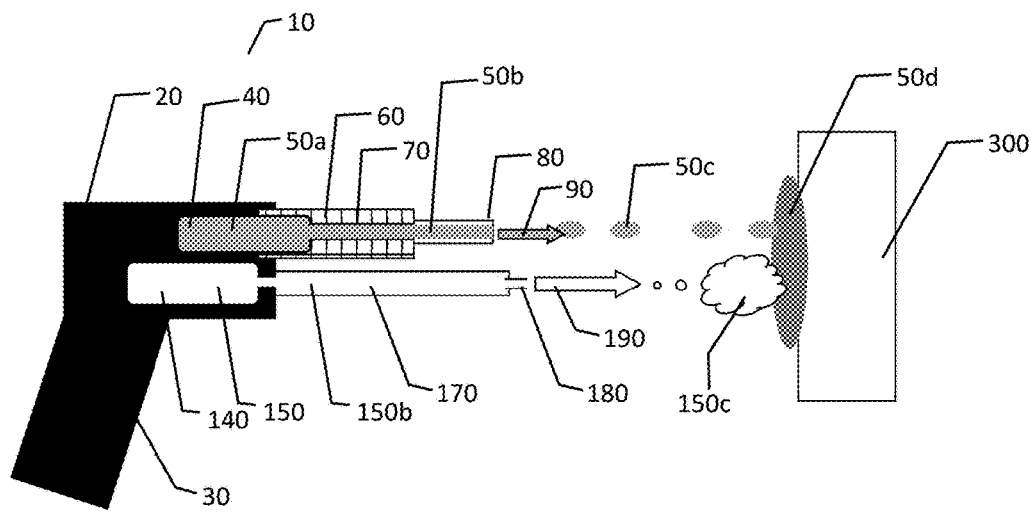
FIG. 1 is a schematic cross-sectional side view of an embodiment of sealant delivery device.

Referring now to FIG. 1, showing a schematic cross-sectional side view of an embodiment of sealant delivery device 10 and target tissue 300, with device 10 generally shaped into a form suitable for hand-held operation, actuation, and targeting, however, in some embodiments device 10 can also be shaped suitably for robotic application as an end-effector on a robotic platform. Device 10 comprises a housing 20 shaped in a grippable unit suitable for manual hand-held operating with a single hand. Optionally, housing 20 can be formed into a pistol or gun-like shape (as shown). Grip 30 is adapted for manual operation for holding/operating device 10.

Inside housing 20 is disposed a sealant compartment 40 containing meltable sealant 50a which is proximal to heater 60. Meltable sealant 50a is in solid or semi-sold form, but upon actuation of the heater 60 proximal to sealant 50a at least a portion of the meltable sealant 50a is melting forming a liquid or semi-liquid sealant 50b which is then advanced through an optionally fully or partially heated channel 70 to an exit nozzle 80, whereby sealant 50 is expressed from nozzle 80 as a stream or droplets (as shown) of molten liquid or semi-liquid sealant 50c as shown by arrow 90. When directed towards tissue or bone surface 300, molten liquid or semi-liquid sealant 50c is then solidifying thus forming a solid or semi-solid film or coating 50d of the surface 300 thus occluding surface 300 of tissue and/or bone and developing a seal preventing further bleeding.

Sealant compartment 40 containing meltable sealant 50 can be in any suitable form. In one embodiment, sealant compartment 40 comprises a compartment filled with granulated solid sealant 50, said compartment being proximal to heater 60 so that upon energizing of heater 60, sealant 50 inside sealant compartment 40 is melting. In this embodiment, sealant compartment 40 is configured with a mechanism to express or advance molten sealant 50b by applying pressure to sealant 50 or to sealant compartment 40. In an alternative embodiment, granulated solid sealant 50 is advanced by mechanical means, by applying pressure to granulated sealant 50 such as with a piston or screw moveable within sealant compartment 40.

In yet another embodiment, sealant 50 is in a form of a rod or stick that is configured for an advancement through heater 60 or within close proximity to heater 60 to effect melting of sealant 50.

In still another embodiment (not shown), a pressure of gas is exerted on sealant compartment 40 causing expression of sealant 50b, 50c.

Other potential designs of sealant compartment 40 of sealant 50 and mechanisms of melting and expressing molten sealant 50b, 50c are possible and will be within the skilled artisan area of expertise.

Figure 2:
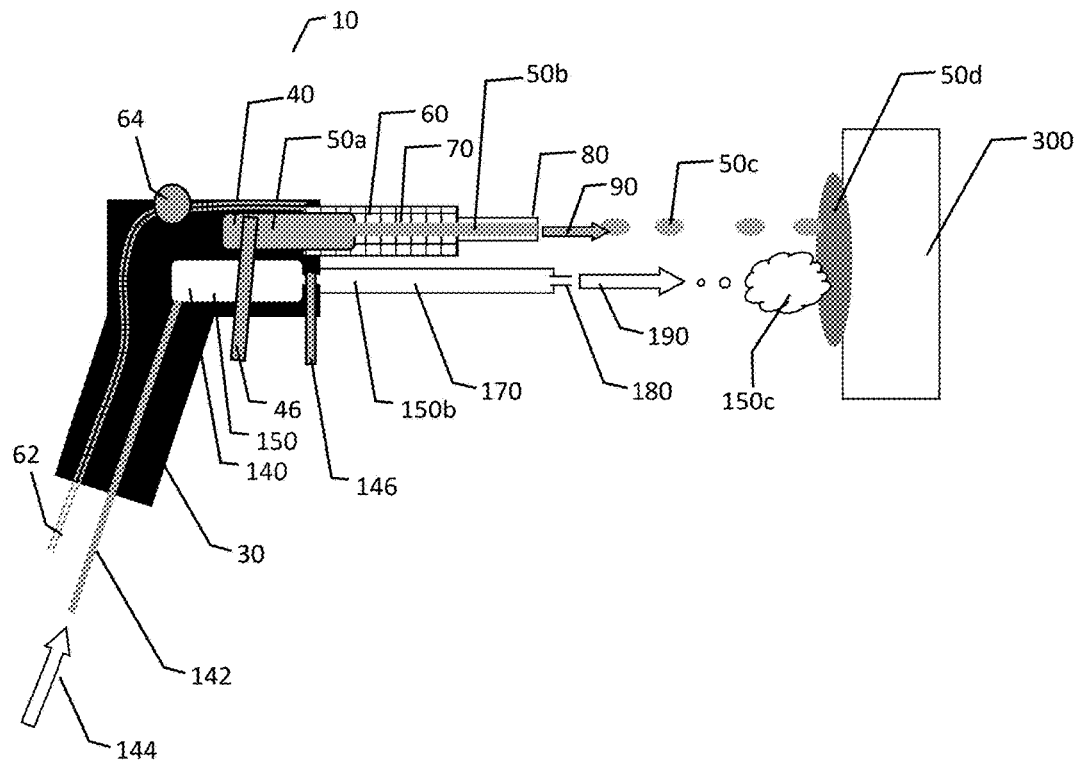
FIG. 2 is a schematic cross-sectional side view of an embodiment of sealant delivery device.

Also referring now to FIG. 2, showing a schematic cross-sectional side view of an embodiment of sealant delivery device 10 and tissue 300, an actuator 46 of expression of molten sealant 50b, 50c is provided to effect expression of molten sealant, with actuator 46 positioned on housing 20 and configured to express molten sealant 50b, 50c as needed by depressing actuator 46. Actuator 46 applies pressure to sealant 50 or to sealant compartment 40 and effects advancement of sealant 50a towards nozzle 80 and expression of molten sealant 50b, 50c from nozzle 80. Actuator 46 can be of trigger lever type and positioned for convenient operation by a finger of the same hand that holds device 10. In one embodiment, each depression of actuator 46 results in a defined quantity of sealant 50 expressed, such as 0.5, 1, 2, 3, 5 $cm^3$ expressed with each depression of actuator 46.

Heater 60 is of any suitable design, such as electrically powered resistance heater, IR heater, induction heater, microwave heater, radiofrequency heater, ultrasonic heater, or similar. The heat transfer from heater 60 to sealant 50 is by conduction, convection, infra-red irradiation, electromagnetic wave, induction heating, etc. Sealant 50 can be heated directly or by transfer of heat from another member heated by heater 60.

Source of energy for heater 60 can be a power supplied via electrical cable 62 (FIG. 2) from outside of device 10, or alternatively, a battery located in the housing 20 (not shown). An optional electric switch 64 can be used to activate heater 60. Electric switch 64 can be any electrical on/off switch and can be located anywhere on housing 20 or outside. In an alternative embodiment, the source of heat can be a chemical reaction, such as a heating pack with e.g. iron oxidation as a heat producing chemical reaction.

The temperature of molten sealant is from about 40° C. to about 100° C., more preferably from 50 C to 80° C., such as 55, 60, 65, 70° C.

Inside housing 20 is also disposed a gas compartment 140 containing cooling gas 150 which is in fluid communication with gas expression port 180 via gas channel 170. Upon actuation of cooling gas 150 expression from device 10, cooling gas 150b advances through channel 170 and is expressed as a gas stream 150c as shown schematically by arrow 190 from gas expression port 180. Advantageously, cooling gas 150c is generally directed into the same direction or towards the same area as molten liquid or semi-liquid sealant 50c. It is achieved by having exit nozzle 80 and gas expression port 180 pointing generally in the same direction, as shown in FIGS. 1 and 2.

In one embodiment (as shown), exit nozzle 80 and gas expression port 180 are parallel to each other and are positioned in close proximity to each other, such as within distance of 0.5-2 cm. Cooling gas 150c is then advancing generally parallel to molten liquid or semi-liquid sealant 50c towards surface 300.

Figure 3:
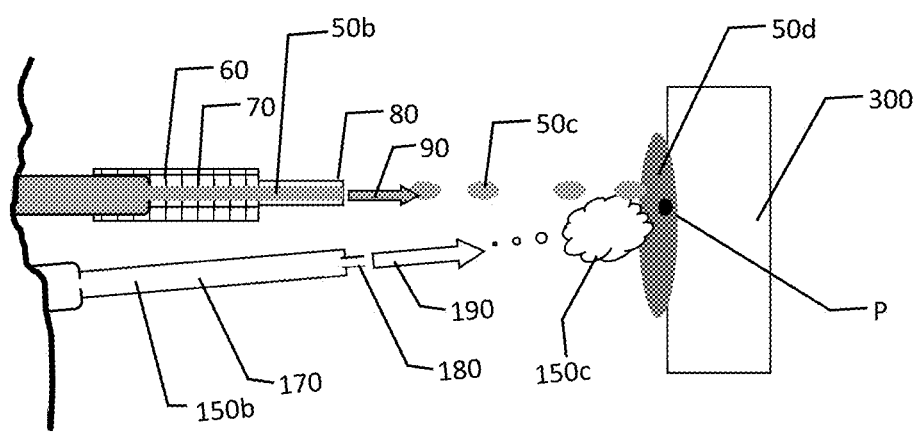
FIG. 3 is a schematic cross-sectional side view of a distal portion of an embodiment of sealant delivery device.

An alternative embodiment, and referring to FIG. 3, presenting a schematic cross-sectional side view of only a distal portion of an embodiment of device 10 as well as target tissue 300, showing sealant delivery device 10 portions representing areas close to exit nozzle 80 and gas expression port 180. As shown, exit nozzle 80 and gas expression port 180 are positioned not parallel to each other, but directed towards the same convergent point or area P at a distance from about 2 cm to about 20 cm, such as 3, 5, 9, 10, 12 cm. In these embodiments, an angle between the directions of exit nozzle 80 and gas expression port 180 is not zero as in case of parallel positioning, but from about 3 to about 30 degrees, such as 5, 10, 15 degrees.

Gas compartment 140 containing cooling gas 150 can be supplied by any source of gas that is capable of supplying a stream of cooling gas though gas expression port 180. In one embodiment, a source of pressurized gas, such as gas cartridge exemplified by gas compartment 140, is located inside housing 20. Temperature of gas 150 is either ambient temperature, such as from about 15 to about 25° C., more preferably around 20° C., or lower, such as from 5 to 15° C., such as 10° C., with cooling achieved due to gas 150 expansion (adiabatic expansion) upon exit from the pressurized cartridge. Gas 150b, 150c can be also cooled by using Vortex Cooling Tubes such as Exair tubes. In one embodiment, there is a further cooling element (such as Peltier element or similar) (not shown) located proximal to channel 170 and providing further gas 150b, 150c cooling.

In another embodiment, there is provided a gas pump or gas fan (not shown) inside housing 20. Such gas pump or fan can be driven by internal battery or by an external power line, and will provide a stream of cooling gas into gas compartment 140.

In an alternative embodiment, pressurized gas 150 is supplied from outside of housing 20 into gas compartment 140 via a gas conduit 142 (FIG. 2) connected to housing 20, with the direction of gas flow shown by arrow 144. Temperature of gas 150b, 150c is either ambient temperature, or lower, with cooling achieved due to gas 150 expansion (adiabatic expansion) upon exit from the pressurized cartridge. Gas 150b, 150c can be also cooled by using Vortex Cooling Tubes such as Exair tubes.

An optional gas switch 146 can be positioned on housing 20 to enable actuating and/or stopping cooling gas 150b, 150c delivery as needed.

Pressure of cooling gas 150 is from about 1.1 atmosphere (atm) to about 5 atm. The rate of gas flow from gas expression port 180 can vary depending upon distance from gas expression port 180 to surface 300, with further distance allowing for higher gas flow, while avoiding disturbing layer of molten sealant 50c and also avoiding embolic effects. In some embodiments, gas 150c exits gas expression port 180 at the rate of 3-100 cm3/s, such as 5, 10, 25 cm3/s.

The gas can be air, nitrogen, argon, carbon dioxide, and combinations thereof, or any suitable cooling gas.

The flow of cooling gas 150 is configured to effect immediate cooling and solidification of molten sealant 50c deposited on tissue 300. In some embodiments, flow of cooling gas 150 directed onto deposited molten sealant 50c is configured to result in solidification of sealant 50c into sealant 50d within 1-10 seconds, more preferably within 1-6 s, such as within 2-5s. In addition, the gas may push the molten material into the tissue pores as it is being solidified to increase surface contact between the sealant and the tissue. For example, the molten material can be pushed by gas deeper into the cut bone surface pores, which increase the grip of the solidified sealant and increase the mechanical sealing abilities.

Figure 4:
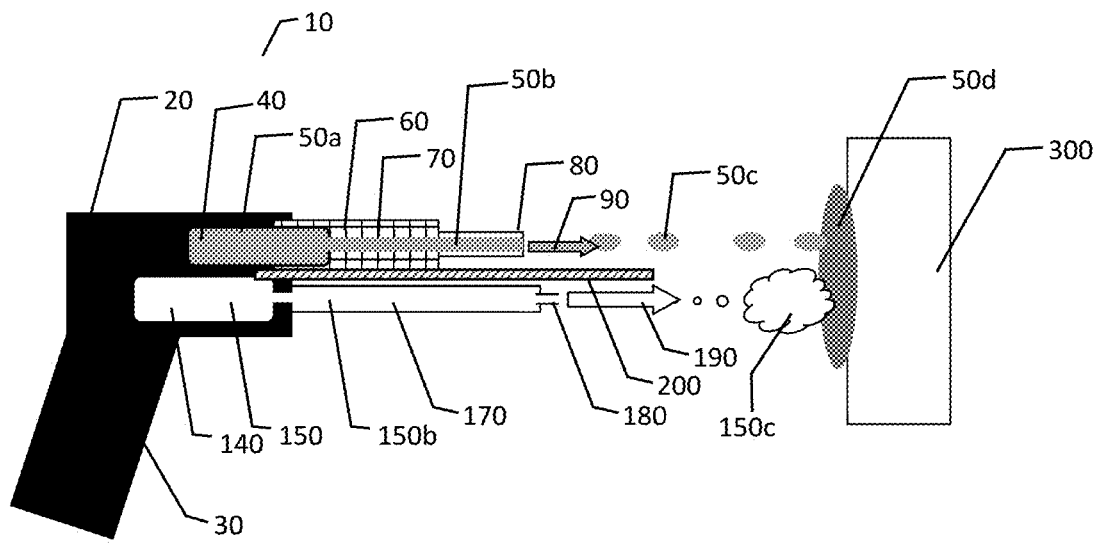
FIG. 4 is a schematic cross-sectional side view of an embodiment of sealant delivery device.

Device 10 is configured so that cooling gas 150c preferably does not interact with molten sealant 50c prior to molten sealant reaching surface of tissue 300, thus avoiding premature cooling of sealant 50c and disrupting flow of sealant 50c towards target tissue 300. Referring also to FIG. 4, showing a schematic cross-sectional side view of an embodiment of sealant delivery device 10 and target tissue 300, in one embodiment, an optional separator or shield 200 comprising a thin elongated strip extending from housing 20 is positioned between stream of molten liquid or semi-liquid sealant 50c expressed from nozzle 80 as shown by arrow 90 and gas stream 150c expressed from gas expression port 180 as shown schematically by arrow 190. Separator 200 extends distally from housing 20 beyond nozzle 80 and gas expression port 180 to prevent premature cooling of sealant 50c by expanding gas stream 150c, prior to sealant 50c reaching surface 300 or immediate proximity of surface 300.

The length of separator 200 extension beyond gas expression port 180 and or nozzle 80 is at least 2 cm, such as from 2 to 10 cm, such as 3, 4, 5 cm. The width of separator 200 in the area between gas expression port 180 and or nozzle 80 and extending distally towards surface 300 is from 1 to 5 cm, such as 2, 3 cm wide.

In some embodiments, separator 200 is retractable/extendable and can be extended distally to project longer of shorter, depending upon distance from gas expression port 180 and nozzle 80 to surface 300. In some embodiments, separator 200 is extended so that there is a distance of about 0.5 to about 3 cm from separator 200 to surface 300, such as 1, 2, 3 cm distance.

Figure 5:
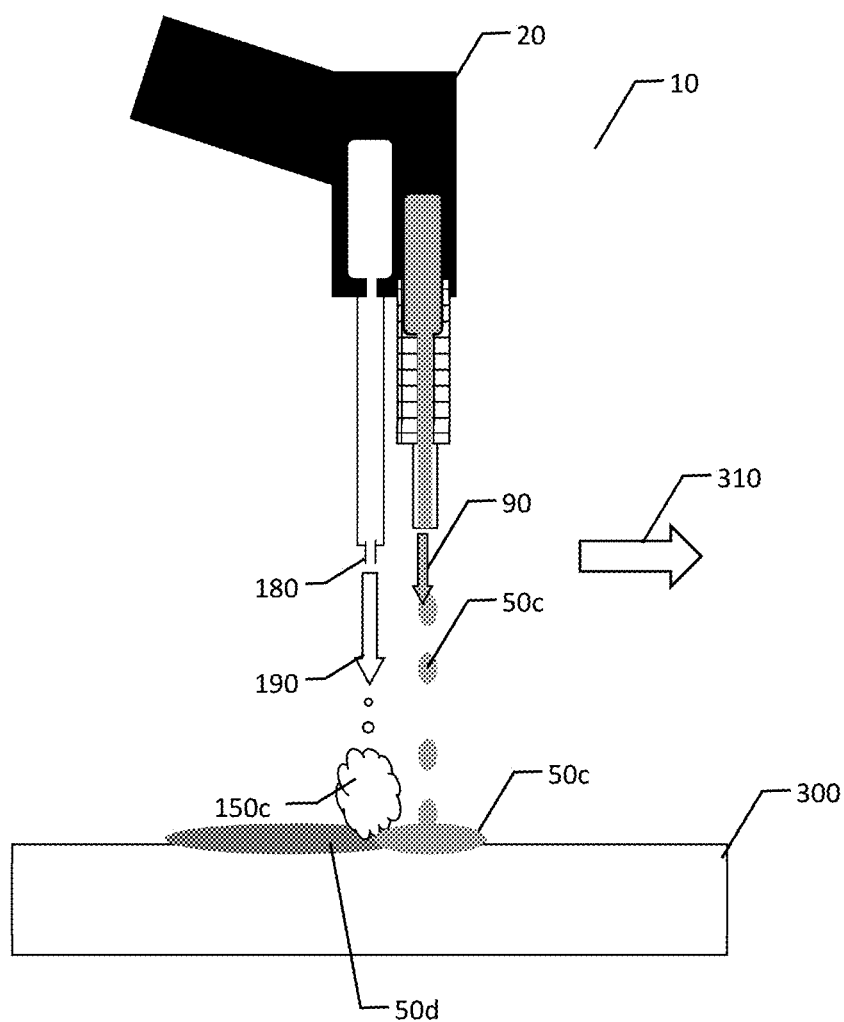
FIG. 5 is a schematic cross-sectional side view of an embodiment of sealant delivery device.

In operation, and referring now to FIG. 5, showing a schematic cross-sectional side view of an embodiment of sealant delivery device 10 and target tissue 300, device 10 is directed with gas expression port 180 and nozzle 80 facing towards surface 300. In some embodiments, it is preferably directed downwards i.e. perpendicular to the ground (as shown), or perpendicular to the ground ±30 degrees, while surface 300 aligned horizontally (as shown) or aligned horizontally ±30 degrees.

Heater 60 is actuated and sealant 50 is at least partially molten. Molten sealant is then expressed towards surface 300 and simultaneously cooling gas is directed towards surface 300 areas where molten sealant is being deposited. As device 10 is advanced across surface 300 (as shown by arrow 310), newly deposited molten sealant 50c is then cooled by gas stream 150c immediately solidifying sealant of surface 300 as solidified sealant 50d.

Advantageously, molten/liquid sealant 50c is immediately cooled by cooling gas 150c and solidified on surface 300 forming solidified sealant 50d, eliminating undesirable run-offs and drips of sealant 50c. Also advantageously, immediate cooling by cooling gas 150c reduces potential for thermal injury to tissue surface 300 from hot sealant 50c. Advantageously, sealant 50c can have in some embodiments relatively high temperature as sealant 50c is immediately cooled upon deposition thus reducing potential for thermal injury to tissue 300, especially when tissue 300 is bone. In some embodiments, sealant 50c has temperature of 80-200° C., such as 80, 90, 100, 125, 150° C.

In operation, molten sealant 50c is deposited on surface 300, with cooling gas 150c directed to:

a) Areas where molten sealant 50c is about to be deposited, for pre-cooling of these areas, and/or b) Areas where molten sealant 50c was already deposited, for cooling and solidifying sealant 50c forming solidified sealant 50d, and/or c) Areas where molten sealant 50c is being deposited, for concurrent cooling and solidifying sealant 50c forming solidified sealant 50d.

Thus, cooling gas 150c is directed to surface 300 prior to molten sealant 50c application, and/or after molten sealant 50c application, and/or concurrently and simultaneously with molten sealant 50c application, or in any combinations of these modes of application.

Advantageously, cooling gas 150c can also be used to remove pooled blood or fluids form the areas where molten sealant 50c is about to be applied. This enables improved contact of molten sealant 50c with tissue surface 300 and better adhesion.

According to further embodiments of the present invention, molten sealant 50c and cooling gas 150c are delivered intermittently and sequentially, so that when molten sealant 50c is delivered, cooling gas 150c is shut off, and vice versa, when cooling gas 150c is delivered, molten sealant 50c is shut off. Such arrangement results in lesser interference of the cooling gas 150c with molten sealant 50c prior to deposition of molten sealant 50c on tissue 300, i.e. prevents blow-off of the molten sealant 50c into undesirable and/or untargeted areas, and prevents premature cooling of molten sealant 50c while the stream 90 of molten sealant 50c is still in transit between nozzle 80 and tissue 300. In some embodiments, cooling gas 150c is not fully shut-off when molten sealant 50c is delivered, but the flow of cooling gas 150c is decreased by at least 50%. In one embodiment, flow of cooling gas 150c when molten sealant 50c is delivered is from 5% to 30%, such as 10%, 20%, 25% of flow of cooling gas 150c when molten sealant 50c is not delivered. In some embodiments, flow of cooling gas 150c when molten sealant 50c is delivered is from 0% to 20% of flow of cooling gas 150c when molten sealant 50c is not delivered.

In some embodiments, half-pressing device 10 control trigger such as actuator 46 is fully stopping or decreasing flow to 0-30% of full flow of cooling gas 150c and full-pressing such control trigger is actuating expression of the molten sealant 50c with no increase in cooling gas 150c flow.

Referring now to FIGS. 6-10, embodiments of delivery device 10a, 10b are presented, whereby delivery of cooling gas 150c is automatically stopped and/or flow of gas decreased when delivery of molten sealant 50c is initiated.

Figure 6:
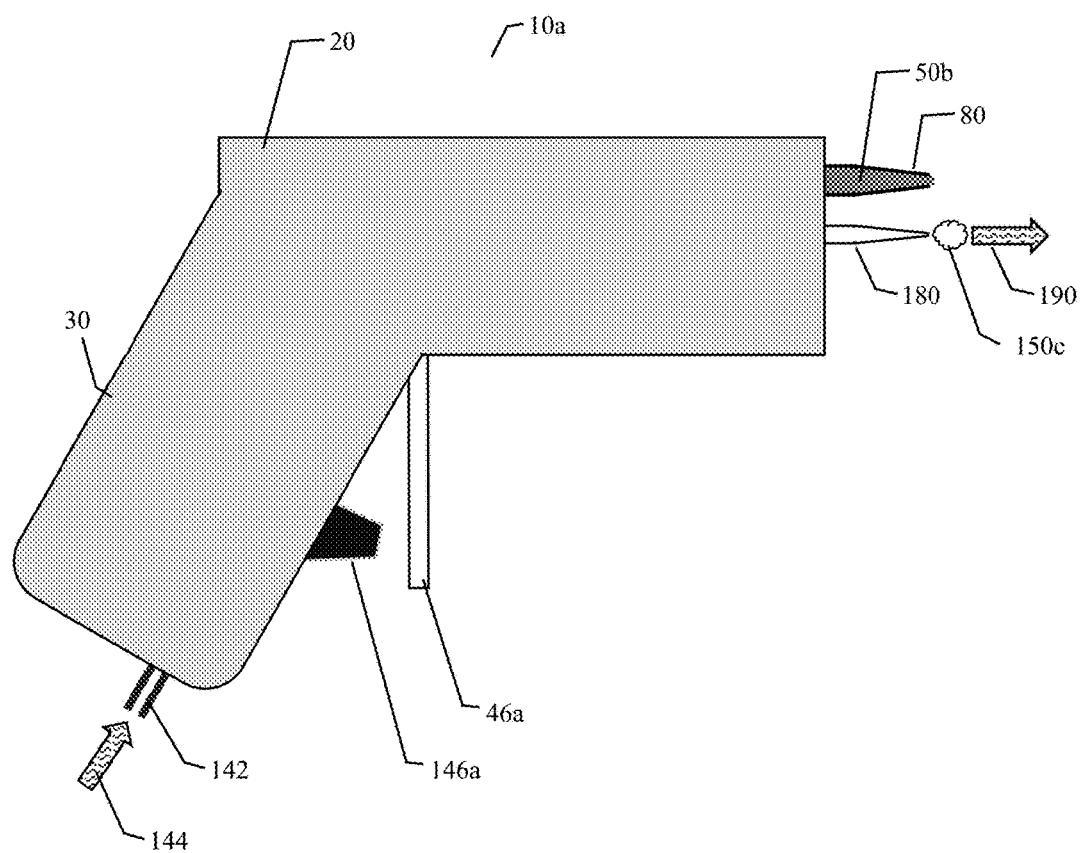
FIG. 6 is a schematic side view of an embodiment of sealant delivery device.

Referring to FIG. 6, showing a schematic side view of an embodiment of sealant delivery device 10a, having housing 20, grip 30, meltable sealant forming a liquid or semi-liquid sealant 50b, which is about to be expressed from exit nozzle 80. The position shown in FIG. 6 corresponds to absence of expression of liquid or semi-liquid sealant from exit nozzle 80.

Pressurized gas is supplied from outside of housing 20 via gas conduit 142 with the direction of gas flow shown by arrow 144. The position shown in FIG. 6 corresponds to cooling gas being expressed as a gas stream 150c as shown schematically by arrow 190 from gas expression port 180.

Gas switch 146a positioned on housing 20 on grip 30 and is in a normally open position, i.e. when gas switch 146a is not depressed, cooling gas 150c is expressed as a gas stream 190. Gas switch 146a can be positioned as shown for convenient single hand operation, i.e. on pistol-like grip area convenient for finger actuation.

Actuator 46a of expression of molten sealant 50b, 50c is also positioned on housing 20 on grip 30 as shown for convenient single hand operation, i.e. on pistol-like grip area convenient for finger actuation and is in a normally closed position, i.e. when actuator 46a is not depressed, molten sealant 50b, 50c is not expressed. Preferably, both actuator 46a and gas switch 146a are proximal to each other for convenience in simultaneous and/or sequential actuating. In most preferred embodiment, as shown, depressing of actuator 46a will result in simultaneous depressing of gas switch 146a.

Figure 7:
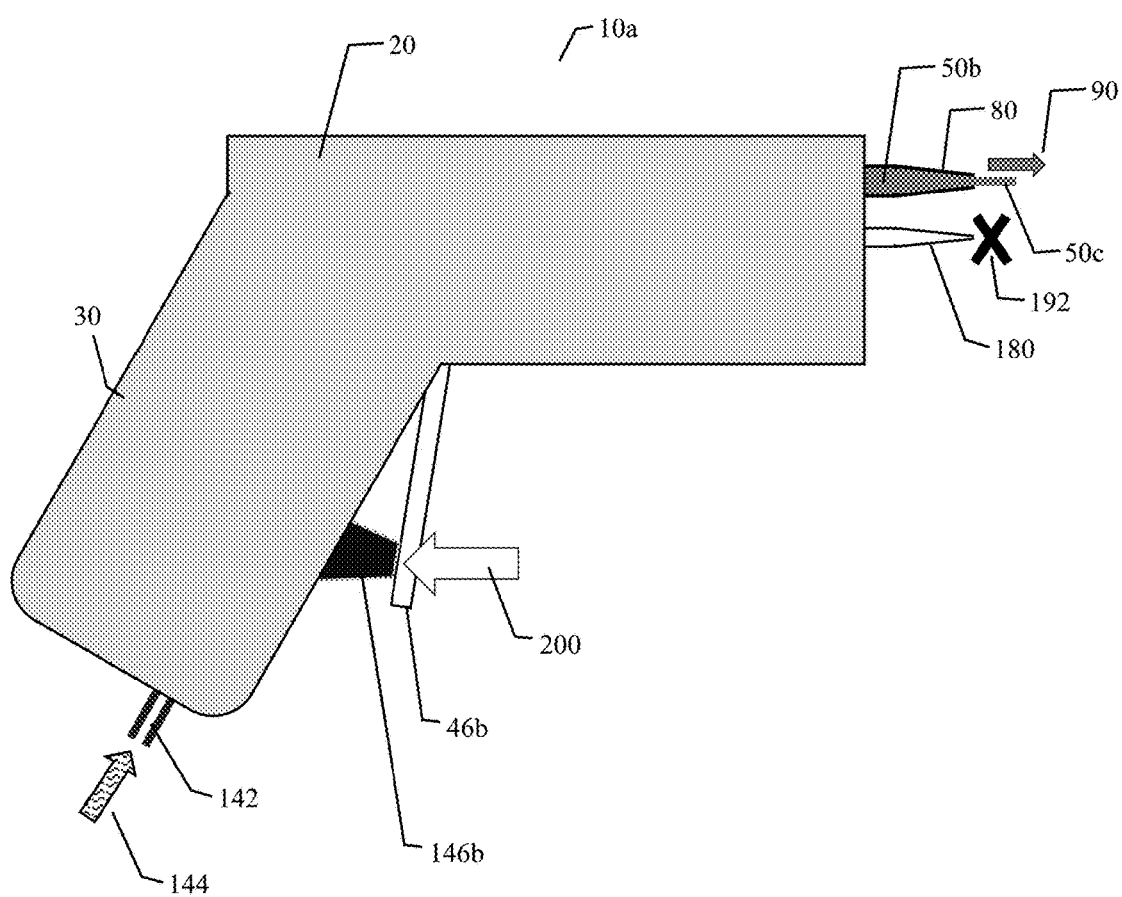
FIG. 7 is a schematic side view of sealant delivery device embodiment of FIG. 6.

Referring now to FIG. 7, showing a schematic side view of sealant delivery device 10a embodiment of FIG. 6, device 10a is shown with actuator 46b depressed as illustrated by arrow 200, thus initiating molten sealant 50c expression from nozzle 80 as shown by arrow 90. As can be seen from FIG. 7, depressing of actuator 46b results in simultaneous depressing of gas switch 146b, resulting in shut-off (or slowdown) of cooling gas expression, as schematically illustrated by symbol "X" with reference numeral 192. Thus, the position shown in FIG. 7 corresponds to little or no cooling gas 150 being expressed, while expression of liquid or semi-liquid sealant 50c from exit nozzle 80 proceeds.

Figure 8:
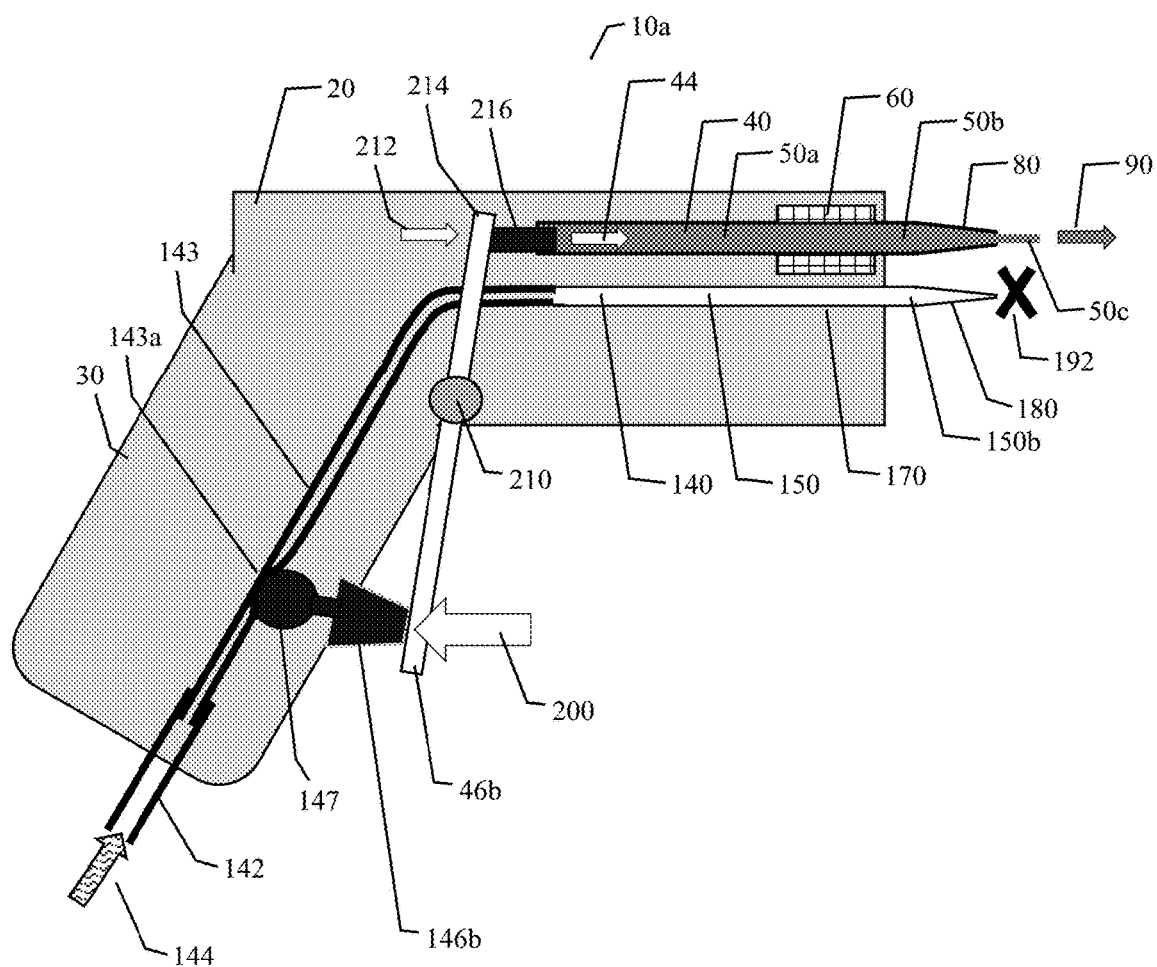
FIG. 8 is a schematic cross-sectional side view of an embodiment of sealant delivery device of FIG. 7 with more detail shown.

Referring now to FIG. 8, showing a schematic cross-sectional side view of an embodiment of sealant delivery device 10a of FIG. 7, more detail is shown to illustrate and enable one potential mechanism whereby delivery of cooling gas 150c is automatically stopped and/or flow of gas decreased when delivery of molten sealant 50c is initiated. As shown in FIG. 8, sealant delivery device 10a is in the position when little or no cooling gas is being expressed as indicated by symbol "X" with reference numeral 192, while expression of liquid or semi-liquid sealant 50c from exit nozzle 80 proceeds.

Pressurized gas is supplied from outside of housing 20 via gas conduit 142 with the direction of gas flow shown by arrow 144. Gas then proceeds through cannula 143 inside housing 20 towards gas compartment 140 containing cooling gas 150. Cannula 143 has a compressible area 143a situated proximal to moveable member 147 that is operatively connected to gas switch 146b. Upon depressing gas switch 146b (shown in depressed position, as indicated by arrow 200), moveable member 147 impinges on compressible area 143a, stopping or significantly decreasing flow of gas 150 through cannula 143 and out of gas expression port 180 gas via channel 170.

Actuator 46b of expression of molten sealant 50c is shown positioned on housing 20 proximal to gas switch 146b, and configured to depress gas switch 146b when actuator 46b is actuated, as shown by arrow 200. Actuator 46b is represented by an elongated trigger lever that is partially rotatable about fixating pin 210 positioned between the ends of elongated trigger lever as shown. Upon depressing one end of actuator 46b trigger lever that is proximal to gas switch 146b as shown by arrow 200, opposite end 214 of actuator 46b trigger lever is moving in an opposite direction as shown by arrow 212, whereby opposite end 214 of actuator 46b trigger lever is pushing on piston 216 that is advancing into sealant compartment 40 containing meltable sealant 50 causing sealant 50a advance towards heater 60 as shown by arrow 44 and move towards nozzle 80 as molten sealant 50b and out of nozzle 80 as molten sealant 50c, shown by arrow 90.

Thus, the embodiment presented in FIG. 8 shows mechanism of device 10a operation, whereby depressing actuator 46b is depressing gas switch 146b, stopping or slowing gas flow from out of gas expression port 180 gas via channel 170 and concurrently advancing expression of molten sealant 50c out of nozzle 80.

Figure 9:
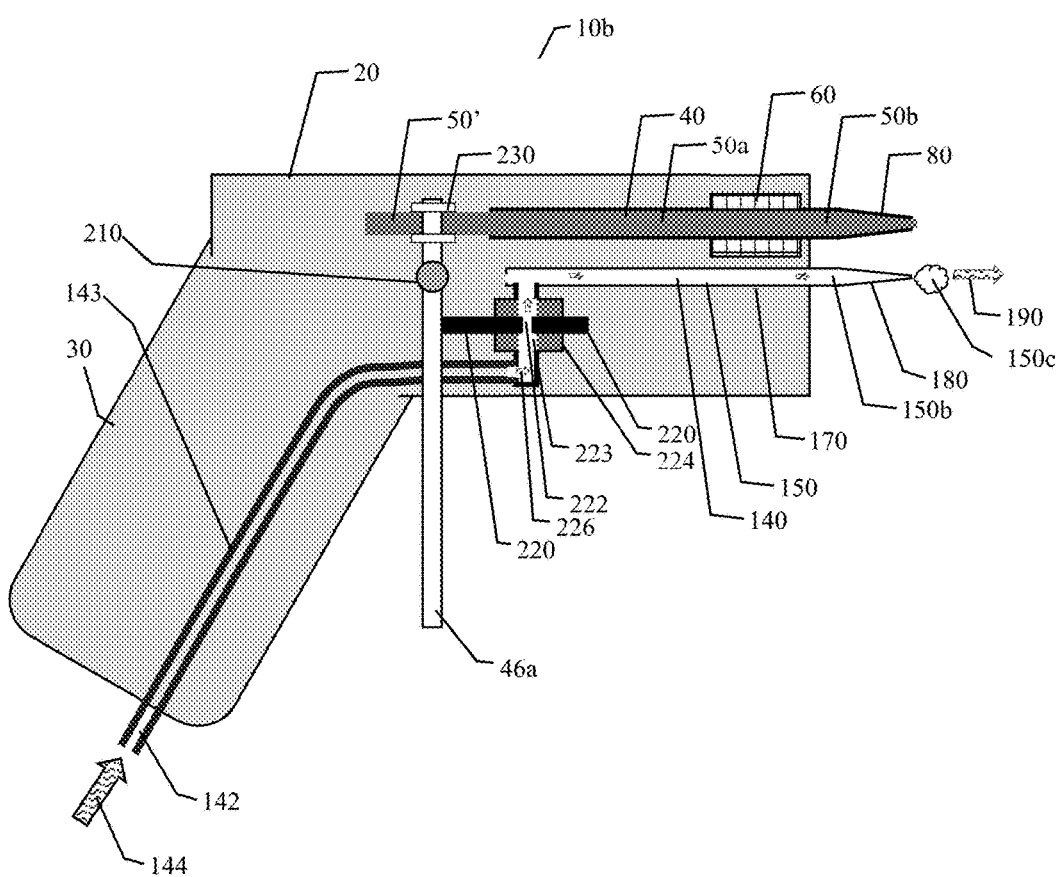
FIG. 9 is a schematic cross-sectional side view of an embodiment of sealant delivery device.

Referring now to FIG. 9, showing a schematic cross-sectional side view of another embodiment of sealant delivery device 10b, whereby delivery of cooling gas 150c is automatically stopped and/or flow of gas decreased when delivery of molten sealant 50c is initiated and delivery of cooling gas 150c is automatically resumed or continued when delivery of molten sealant 50c is interrupted or stopped.

The position shown in FIG. 9 corresponds to cooling gas being expressed as a gas stream 150c as shown schematically by arrow 190 from gas expression port 180. The position shown in FIG. 9 further corresponds to absence of expression of liquid or semi-liquid sealant 50b, 50c from exit nozzle 80.

Pressurized gas is supplied from outside of housing 20 via gas conduit 142 with the direction of gas flow shown by arrow 144. Gas then proceeds through cannula 143 inside housing 20 towards entrance 223 of gas valve 224, with a slidable gas control rod 220 with aperture 222 in gas control rod 220 providing path for gas to advance into gas compartment 140 containing cooling gas 150 as shown by arrows 226. With aperture 222 aligned with entrance 223 of gas valve 224 cooling gas is being expressed as a gas stream 150c.

Actuator 46a of expression of molten sealant 50c is shown positioned on housing 20 being operatively connected to slidable gas control rod 220. Actuator 46a is represented by an elongated trigger lever that is partially rotatable about fixating pin 210 positioned between the ends of elongated trigger lever as shown.

First end of elongated trigger lever is positioned outside of housing 20 and configured for manual actuation or depressing. The opposite end of elongated trigger lever of actuator 46a is engaged with a solid sealant rod 50' via engagement member 230.

Figure 10:
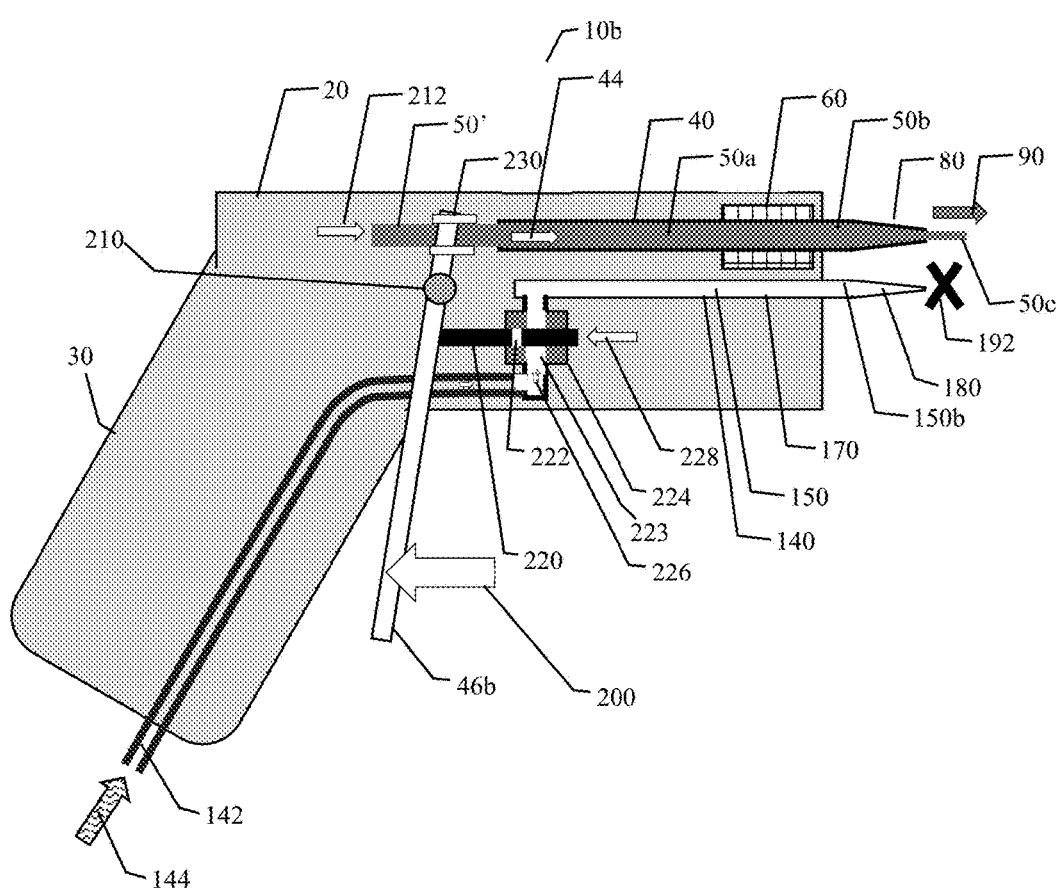
FIG. 10 is a schematic cross-sectional side view of sealant delivery device of the embodiment of FIG. 9.

Referring now to FIG. 10, showing a schematic cross-sectional side view of the embodiment of FIG. 9, the position shown corresponds to no cooling gas or only a small quantity of cooling gas being expressed, as indicated by symbol "X" designated with numeral 192. The position shown in FIG. 10 further corresponds to expression of liquid or semi-liquid sealant 50c from exit nozzle 80, as indicated by arrow 90.

Upon depressing the first end of actuator 46b trigger lever that is outside of housing 20, as shown by arrow 200, opposite end of actuator 46b trigger lever is moving in an opposite direction as shown by arrow 212, whereby it is advancing solid sealant 50' which can be in a form of a rod or a stick via engagement member 230 in the direction of compartment of sealant 40 as shown by arrow 44, causing sealant 50a advance towards heater 60 and move towards nozzle 80 as molten sealant 50b and out of nozzle 80 as molten sealant 50c, shown by arrow 90.

The depression of the first end of actuator 46b trigger lever that is outside of housing 20, as shown by arrow 200 simultaneously causes slidable gas control rod 220 move within gas valve 224, as shown by arrow 228, resulting in aperture 222 in gas control rod 220 losing alignment with entrance 223 and closing path for gas to advance into gas compartment 140. With aperture 222 not aligned with entrance 223 of gas valve 224, no cooling gas is being expressed from port 180.

Thus, the embodiments presented in FIGS. 9-10 show another mechanism of device 10b operation, whereby depressing actuator 46b is blocking gas flow from out of gas expression port 180 gas via channel 170 and concurrently advancing expression of molten sealant 50c out of nozzle 80.

In operation of embodiments of FIGS. 6-10, health care practitioner directs device 10a, 10b nozzle 80 and gas expression port 180 towards tissue 300, optionally uses gas flow 190 out of gas expression port 180 to pre-cool tissue 300 and to remove some excess fluids from surface of tissue 300, then depresses actuator 46b thus blocking gas flow, concurrently advancing expression of molten sealant 50c out of nozzle 80 onto tissue 300. Consequently, health care practitioner releases actuator 46a thus initiating gas flow and concurrently stopping expression of molten sealant 50c out of nozzle 80. The health care practitioner then uses gas flow 190 directed at just deposited molten sealant and impinging on the molten sealant on surface 300 to effect immediate cooling of molten sealant 50d on tissue 300.

In some embodiments (not shown), gas expression port 180 and nozzle 80 are positioned on elongated connectors and are distal to housing 20 and thus adapted for laparoscopic operation through a trocar, i.e. for insertion of gas expression port 180 and nozzle 80 through a trocar.

Figure 11:
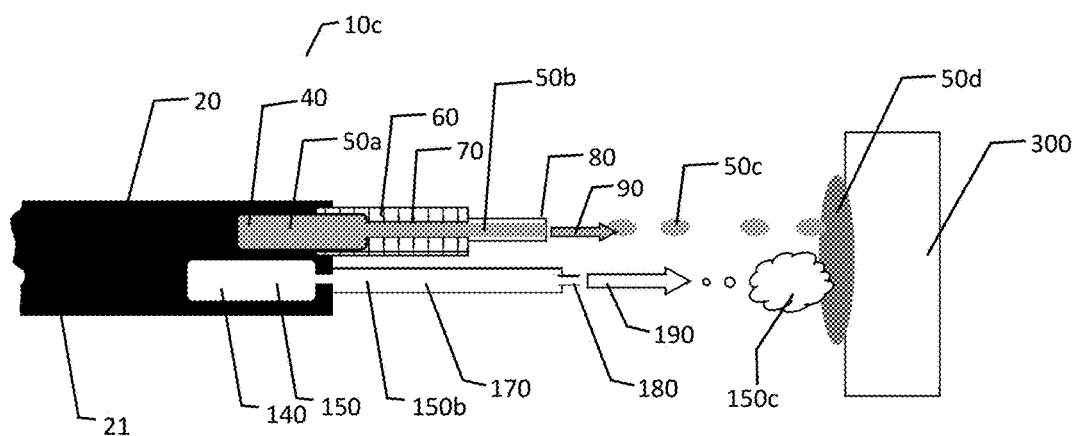
FIG. 11 is a schematic cross-sectional side view of an embodiment of the delivery device mounted on a robotic arm as an end-effector.

Referring now to FIG. 11, showing a schematic cross-sectional side view, an embodiment of the delivery device is shown mounted on a robotic arm 21 as an end-effector 10c, having similar construction as shown in FIG. 1 and following figures, but configured for robotic operation and not a hand-held operation, whereby triggering and activating of delivery of molten sealant 50c and cooling gas 150c is performed by electronic activation of corresponding valves and levers (not shown).

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims.

We claim:

1. A device for delivering a sealant to a tissue, comprising:
   a) a sealant compartment,
   b) a cooling gas compartment, and
   c) a heater, all disposed inside a unified housing; wherein the sealant is liquid, semi-liquid or molten and flowable; wherein said sealant compartment expresses the sealant in a flowable form from said device via an exit nozzle; wherein said gas compartment expresses a cooling gas via a gas expression port; wherein said exit nozzle and said gas expression port are co-directed to a first direction, said device configured so that the cooling gas does not interact with the sealant prior to the sealant reaching the tissue, said device further configured for avoiding disrupting a flow of the sealant towards the tissue.

2. The device of claim 1, wherein said sealant comprises a wax, a hemostatic wax, a bone wax, a bone putty, and combinations thereof.

3. The device of claim 1, wherein said sealant is selected from the group consisting of polyethylene glycol, beeswax, calcium stearate, alkylene oxide copolymers, isopropyl palmitate, paraffin, petroleum jelly, oxidized regenerated cellulose powder (ORC), oxidized cellulose powder (OC), gelatin powder, starch powder, chitosan powder, and combinations thereof.

4. The device of claim 1, wherein said sealant has a melting point from about 40° C. to about 100° C.

5. The device of claim 1, wherein said housing can be held with one hand.

6. The device of claim 1, wherein triggering and activation of delivery of molten sealant and cooling gas is caused by at least one electronic activation of corresponding valves and levers.

7. The device of claim 1, wherein said heater is powered by a battery positioned inside said housing, or by an external power supply.

8. The device of claim 1, wherein said cooling gas is supplied by a fan or a pump mounted inside said housing, or by an internal source of compressed gas mounted inside said housing, or by an external source of compressed gas.

9. The device of claim 1, further comprising a separator that is a thin elongated strip extending from said housing into said first direction and positioned between said sealant in said flowable form being expressed from said exit nozzle and said cooling gas being expressed via said gas expression port, wherein said separator extends distally from said housing beyond said exit nozzle and said gas expression port in said first direction.

10. The device of claim 1, wherein said exit nozzle and said gas expression port are directed parallel to each other.

11. The device of claim 1, wherein said exit nozzle and said gas expression port are directed angular to each other, and wherein said sealant in said flowable form that is expressed from said exit nozzle and said cooling gas that is expressed via said gas expression port converge on a target located in said first direction and distal from said exit nozzle and said gas expression port.

12. The device of claim 1, wherein said cooling gas expressed via said gas expression port cools and solidifies said molten sealant deposited on said tissue within 1-10 seconds.

13. The device of claim 1, wherein said cooling gas expressed via said gas expression port pushes said molten sealant into pores of said tissue thus increasing a surface contact between the sealant and the tissue.

14. The device of claim 1, further comprising an actuator operatively connected to said sealant compartment and configured upon depressing to activate expressing the sealant via said exit nozzle; and a gas switch operatively connected to said gas compartment and configured for activating expressing said cooling gas via said gas expression port.

15. The device of claim 14, wherein said actuator is operatively connected to said gas switch, wherein depressing said actuator simultaneously operates said gas switch, whereby said gas switch at least partially blocks expressing said cooling gas via said gas expression port.

16. The device of claim 15, wherein half-pressing said actuator at least partially blocks expressing said cooling gas and full pressing said actuator activates expressing the sealant via said exit nozzle.

17. The device of claim 15, wherein releasing said actuator simultaneously operates said gas switch, whereby said gas switch opens expressing said cooling gas via said gas expression port.

18. The device of claim 15, wherein said actuator is normally closed and said gas switch is normally open.

19. A method of delivering the sealant to the tissue, comprising:
 a) Actuating the device of claim 1 for delivery of said molten sealant to said tissue;
 b) Depositing said molten sealant onto said tissue;
 c) Optionally stopping delivering of said molten sealant to said tissue;
 d) Actuating delivery of said cooling gas to said molten sealant on said tissue; and
 e) Cooling and solidifying said molten sealant on said tissue.

* * * * *